United States Patent
Zwick et al.

(10) Patent No.: US 8,195,275 B2
(45) Date of Patent: Jun. 5, 2012

(54) VESSEL SIZE IMAGING FOR ANTIANGIOGENIC THERAPY

(75) Inventors: Stefan Zwick, Heidelberg (DE); Ralph Strecker, Erlangen (DE); Fabian Kiessling, Heidelberg (DE); Arne Hengerer, Erlangen (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 919 days.

(21) Appl. No.: 12/124,681

(22) Filed: May 21, 2008

(65) Prior Publication Data

US 2008/0294035 A1    Nov. 27, 2008

Related U.S. Application Data

(60) Provisional application No. 60/939,748, filed on May 23, 2007.

(51) Int. Cl.
*A61B 5/055* (2006.01)
*G06K 9/00* (2006.01)

(52) U.S. Cl. ........................ 600/420; 382/128
(58) Field of Classification Search ................. 600/410, 600/420, 504; 382/128; 324/307; 345/424
See application file for complete search history.

(56) References Cited

U.S. PATENT DOCUMENTS

| | | | | |
|---|---|---|---|---|
| 5,128,121 | A | * | 7/1992 | Berg et al. ..................... 424/9.32 |
| 6,951,541 | B2 | * | 10/2005 | Desmarais ..................... 600/437 |
| 7,317,821 | B2 | * | 1/2008 | Chen et al. ..................... 382/130 |
| 7,744,854 | B2 | * | 6/2010 | Rustum et al. ................. 424/9.3 |

OTHER PUBLICATIONS

Tropres I, Grimault S, Vaeth A, Grillon E, Julien C, Payen JF, Lamalle L, Decorps M. Vessel Size Imaging. Magnetic Resonance in Medicine 2001; 45:397-408.*

* cited by examiner

*Primary Examiner* — Michael Rozanski
(74) *Attorney, Agent, or Firm* — Lempia Summerfield Katz LLC

(57) ABSTRACT

A system and method of evaluating the effectiveness of anti-angionetic therapy is described. A patient or test animal is treated with an antiangionetic substance. Magnetic resonance imaging data is obtained prior to and subsequent to the treatment. The parameters of the imaging process are configured so that, by administering a intravascular contrast agent, the relative size of the microvascular and the total vascular volumes in a region of interest may be obtained, so as to form a vascular size index. The value of the vascular size index and other pharmacokinetic data obtained by the administration of a diffusible contrast agent are used to assess the efficacy of the treatment or the antiangionetic substance being studied.

15 Claims, 2 Drawing Sheets

VESSEL SIZE IMAGING FOR ANTIANGIOGENIC THERAPY

This application claims the benefit of U.S. provisional application Ser. No. 60/939,748, filed on May 23, 2007, which is incorporated herein by reference.

TECHNICAL FIELD

The present application generally relates to the use of magnetic resonance imaging for assessing therapy response. More particularly the application relates to a method for assessing anti-angiogenic therapy.

BACKGROUND

In cancer therapy, anti-angiogenesis is a promising candidate treatment protocol. The basis for tumor growth is angiogenesis; that is the creation of a blood supply to support the growth tumor cells with oxygen and other nutrients. The use of angiogenesis inhibitors (for example, the humanized monoclonal antibody Bevacizumab, trade name AVASTIN from Genentech, South San Francisco, Calif.) causes blood vessel maturation and regression in tumors. By this mechanism, the growth of a tumor can be stopped or slowed in certain circumstances.

The use of angiogenesis inhibitors results in changes in relative blood volume, permeability and perfusion which can be monitored by magnetic resonance imaging (MRI) techniques. However, there is no clinically evaluated surrogate endpoint for anti-cancer therapy regimens. At present, volumetric measurements, such as measurements of the biggest tumor diameter, are used to determine the response of a patient or experimental animal to the therapy. A volumetric measurement, however, does not appear to be sufficiently reliable and nor does such a measurement provide an early assessment of outcome.

Anti-angiogenic tumor therapies (e.g., with AVASTIN) would benefit from stable and early indicators of therapeutic effectiveness. In this context, dynamic contrast enhanced (DCE) MRI in combination with the administration of diffusible contrast agents has proven promising. Applying pharmacokinetic models to the dynamic MRI data, parameter maps with physiological relevant information like transfer constant ($K_{trans}$), extra-vascular extra-cellular volume fraction ($V_e$), or vascular volume fraction ($V_p$) can be calculated. Using user-defined regions-of-interest (ROI), it is possible to calculate and compare quantitative results for specific tissues-of-interest.

The transfer constant $K_{trans}$ has shown to be an early marker of biological response of tumor tissue to anti-angiogenic therapy, but reproducibility studies have shown that changes appear to be obscured by poor reproducibility statistics. Only changes in the range of 50% are considered to be significant in isolation as a reliable assessment of therapeutic effectiveness.

SUMMARY

A method of assessing angiographic therapy is described, the method including placing a subject in a magnetic resonance imaging (MRI) device; administering a blood pool contrast agent; obtaining a MRI image sequence; and determining a vessel size index value.

In an aspect, a system for treating a patient includes a magnetic resonance imaging (MRI) device; and a catheter. The catheter is used to administer an intravascular contrast agent, and the magnetic resonance imaging device is configured to obtain images suitable for performing vascular size imaging analysis.

In yet another aspect, a computer system is disclosed, including a control unit for controlling a magnetic resonance imaging device and obtaining image data sets; a database having a plurality of records, the records containing magnetic resonance image data sets; and, a user interface allowing evaluation of image data sets stored in the database. At least some of the imaging data sets are obtained using an intravascular contrast agent, and the evaluation of the data sets results in the determination of a vessel size index value.

In a further aspect, a computer program product is disclosed, including a computer-usable medium having computer-readable program code recorded thereon, the program code being executable on a computer, to process image data by: applying pharmacokinetic models to a first type of image data; calculating parameters with relevant physiological information from the models; calculating a vessel size index value characterizing a second type of image data; and presenting the physiological information and the vessel size index value at a user interface.

DETAILED DESCRIPTION

Figure 1:
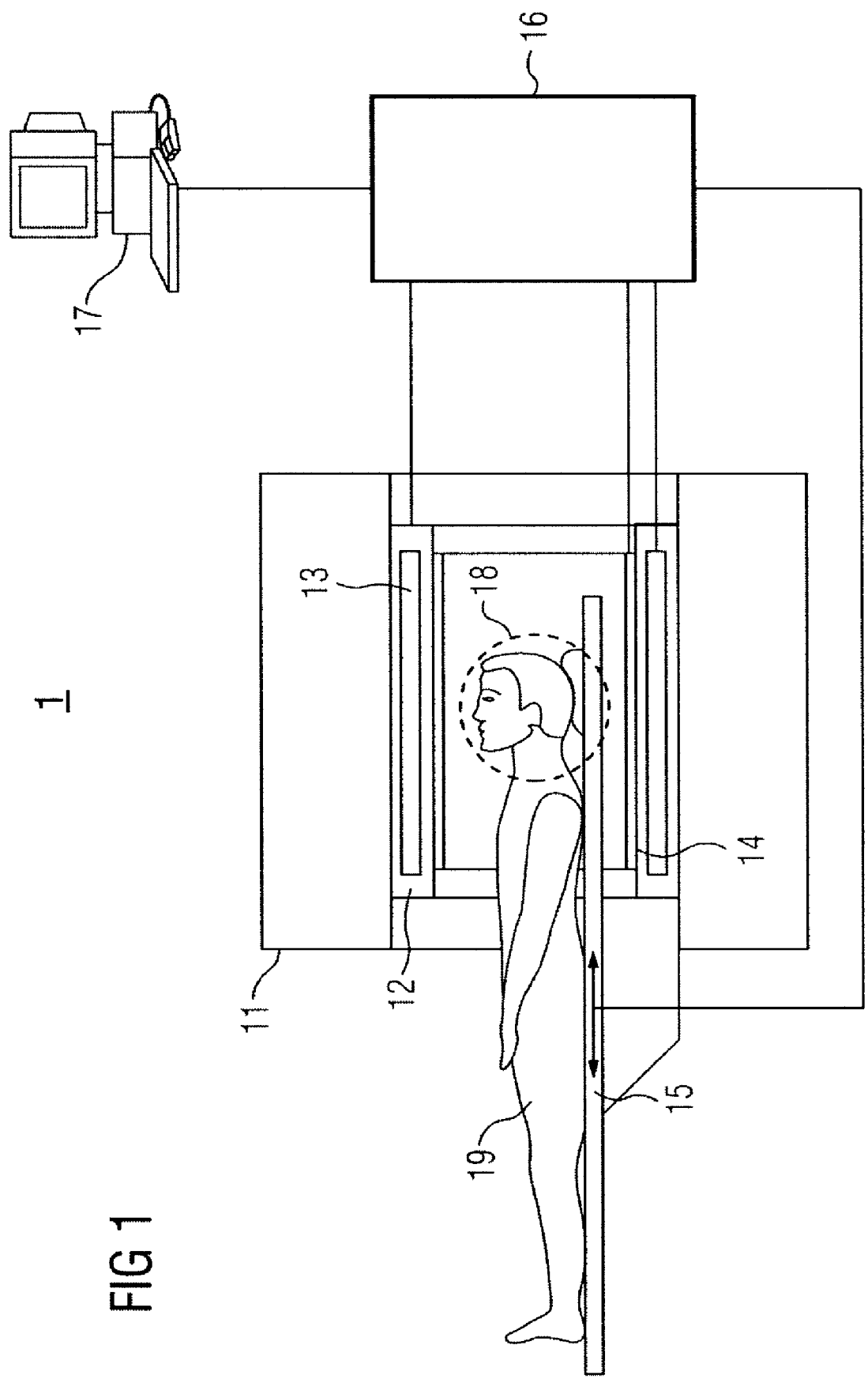
FIG. 1 is a block diagram illustrating an embodiment of the invention.

Exemplary embodiments may be better understood with reference to the drawings, but these embodiments are not intended to be of a limiting nature. Like numbered elements in the same or different drawings perform similar functions.

The combination of hardware and software to accomplish the tasks described herein may be termed a platform, treatment suite, or the like. The instructions for implementing processes of the platform may be provided on computer-readable storage media or memories, such as a cache, buffer, RAM, removable media, hard drive or other computer readable storage media. Computer readable storage media include various types of volatile and nonvolatile storage media. The functions, acts or tasks illustrated or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Some aspects of the functions, acts, or tasks may be performed by dedicated hardware, or manually by an operator.

In an embodiment, the instructions may be stored on a removable media device for reading by local or remote systems. In other embodiments, the instructions may be stored in a remote location for transfer through a computer network, a local or wide area network, by wireless techniques, or over telephone lines. In yet other embodiments, the instructions are stored within a particular computer, system, or device.

Where the term "data network", "web" or "Internet", or the like, is used, the intent is to describe an internetworking environment, which may include both local and wide area telecommunications networks, where defined transmission protocols are used to facilitate communications between diverse, possibly geographically dispersed, entities. An example of such an environment is the world-wide-web (WWW) and the use of the TCP/IP data packet protocol, and the use of Ethernet or other known or later developed hardware and software protocols for some of the data paths. Often, the internetworking environment is provided, in whole or in part, as an attribute of the facility in which the platform is located.

Communications between the devices, systems and applications may be by the use of either wired or wireless connections. Wireless communication may include, audio, radio, lightwave or other technique not requiring a physical connection between a transmitting device and a corresponding receiving device. While the communication may be described as being from a transmitter to a receiver, this does not exclude the reverse path, and a wireless communications device may include both transmitting and receiving functions. Such wireless communication may be performed by electronic devices capable of modulating data as a signal on a carrier wave for transmission, and receiving and demodulating such signals to recover the data. The devices may be compatible with an industry standard protocol such as IEEE 802.11b/g, or other protocols that exist, or may be developed.

The terminology associated with the use of a magnetic resonance imaging (MRI) device is specialized to the apparatus and may differ from that used for other imaging modalities. The terms used herein are believed to be, and are meant to be interpreted as, understood by a person of skill in the art at the time of preparation of the specification, unless specifically differentiated herein.

Vessel Size Imaging (VSI) is a method of determining the mean blood vessel size for a tissue volume of interest; for example, a tumor. VSI is based on measuring the magnetic susceptibility differences between blood vessels and surrounding tissues induced by the injection of a superparamagnetic blood pool (intravascular) contrast agent.

Contrast is the relative difference of signal intensities in two adjacent regions of an image. Due to the $T_1$ and $T_2$ relaxation properties in magnetic (MRI) resonance imaging, differentiation between various tissues in the body is possible. Contrast is affected by not only the $T_1$ and $T_2$ values of specific tissues and contrast agents, but also the differences in the magnetic field strength, temperature changes, and many other factors. Contrast relies on the selection of appropriate pulse sequences (spin echo, inversion recovery, gradient echo, turbo sequences and slice profile).

$T_2$ weighted imaging using a spin echo type sequence is only sensitive to the signal arising from the microvascular network whereas $T_2^*$ weighted imaging is sensitive to susceptibility perturbations arising from all sizes of blood vessels ranging from capillaries to major vessels.

A vessel size index d may be calculated from measurements of the transversal relaxation rate changes $\Delta R_2$ and $\Delta R_2^*$ pre- and post-contrast-agent administration. Taking into account a diffusion coefficient D, the gyromagnetic ratio γ (for water protons, γ=42.576 MHz/T), the susceptibility differences between blood vessel and surrounding tissue $\Delta \chi$, and the magnetic field strength $B_0$, d is given by:

$$d = 0.425 \left(\frac{D}{\gamma \Delta \chi B_0}\right)^{1/2} \left(\frac{\Delta R_2^*}{\Delta R_2}\right)^{3/2}. \quad (1)$$

Changes in the relaxation rate $\Delta R_2$ can be calculated from $T_2$ weighted spin echo (SE) measurements by taking the natural logarithm of the relative signal intensities from post- and pre-contrast images, divided by the echo time $T_E$:

$$\Delta R_2 = \frac{1}{T_E} \ln\left(\frac{S_{pre}}{S_{post}}\right) \quad (2)$$

$\Delta R_2^*$ maps may be calculated from the transversal relaxation time $T_2^*$ before and after injection of the contrast agent:

$$\Delta R_2^* = \frac{1}{T_{2_{post}}^*} - \frac{1}{T_{2_{pre}}^*} \quad (3)$$

$T_2^*$ can be measured by acquiring $T_2^*$ weighted multi-echo gradient echo (GRE) images with increasing $T_E$. $\Delta R_2^*$ maps may be obtained by fitting an exponential decay function $T_E$ to each analyzed voxel in the pre-contrast post-contrast $T_2^*$ weighted image series and subtracting the $R_2^*$ fit parameter of the post- and pre-contrast data. For computational purposes, the diffusion constant D may either be assumed to be constant over the whole imaged volume, or taken from apparent diffusion coefficient (ADC) maps obtained from diffusion weighted imaging.

The susceptibility difference $\Delta \chi$ between blood vessels and the surrounding tissue depends on the specific type contrast agent used and is determined for each specific type of contrast agent.

Instead of the susceptibility difference, $\Delta \chi$, the spread of the Larmor frequency $\delta \omega$ at the surface of vessels which are perpendicular to the magnetic field may be determined. Using $\delta \omega$ leads to a slightly different equation to determine the vessel size index d:

$$d = 0.425 \left(\frac{2\pi D}{\delta \omega}\right)^{1/2} \left(\frac{\Delta R_2^*}{\Delta R_2}\right)^{3/2} \quad (4)$$

Both, $\Delta \chi$ and $\delta \omega$ can be determined by filling a hollow ball with blood and the specific contrast agent to be used. The concentration of contrast agent used is related to the concentration used in the VSI measurement. Inside the ball, two water filled capillary tubes are disposed perpendicular to each other. The ball, including the capillaries, may be positioned in an MRI system such that that one of the capillaries is aligned with the magnetic field $B_0$, while the other is orthogonal to $B_0$. By measuring the resonance frequencies inside the two capillaries, $\delta \omega$ can be determined by:

$$\delta \omega = \omega_\| - \omega_\perp \quad (5)$$

where $\omega_\|$ is the resonance frequency of the water inside the parallel capillary and $\omega_\perp$ is the resonance frequency of the water inside the perpendicular capillary to the magnetic field. $\Delta \chi$ can be calculated from $\delta \omega$ by:

$$\Delta \chi = \frac{\delta \omega}{2\pi \gamma B_0}. \quad (6)$$

A method for calculation of vessel size index maps from SE and GRE images is described. Additionally, blood volume (BV) maps can be calculated from the $T_2^*$ weighted pre and post images by:

$$BV = \frac{3}{4\pi} \frac{\Delta R_2^*}{\gamma \Delta \chi B_0}. \quad (7)$$

Vessel Size Imaging may be used to supplement DCE-MRI data. In this context, an increase of the vessel size index d after administering therapy may be interpreted as the destruction of small immature tumor vessels and be consistent the expected changes of tumor visualization after blocking the of vascular endothelial growth factor receptor VEGFR2.

VSI may be combined with DCE-MRI measurements to increase the specificity or sensitivity of the investigation. DCE-MRI analysis software enables the quantitative analysis of the acquired data to obtain functional parameters such as vessel permeability, perfusion and relative blood volume. These parameters may change a relatively short time after beginning the anti-angiogenic therapy, but these parameter changes can also regress during treatment. This occurrence may be explainable by the shrinkage of tumors under therapy, leading to a compartmental shift. In contrast, the VSI changes relatively slowly after the beginning of the therapy and may not be substantially influenced by changes in tumor growth or size. Thus, the parameters obtained by DCE-MRI and VSI may not be highly correlated. By evaluation of the data of DCE-MRI and VSI, control of the therapy can be improved as compared to evaluation of DCE-MRI or VSI data alone.

In another aspect, VSI data based on MRI studies with very small iron oxide particle (e.g. VSOP, from Ferropharm, Berlin, Germany) may evaluated using, for example, a software program product in a Syngo® task card for controlling anti-angiogenic tumor therapy, such as for AVASTIN therapy.

VSOP are super-paramagnetic single-domain nanoparticles with increased $R_1$ relativity and surface-stabilizer substances. These nanoparticles may include iron hydroxide, ferric hydrate, iron oxide, iron mixed oxide or iron; are between 1 and 10 nm in size, have a mean particle diameter of 2-4 nm; and have increased $R_1$ relaxivity of between 2 and 50, the ratio of the relaxivities $R_2/R_1$ being less than 5. Typically, stabilizer substances such as carboxylic acids may be bound to the particle surfaces; these stabilizers inhibit aggregation and sedimentation of the particles under gravity force or in a magnetic field. The particles can also contain further known stabilizer substances and other pharmacological substances.

VSOP in this use, when compared with to low molecular weight gadolinium chelates, is characterized by the substantial absence of extravasation of this blood-pool contrast medium into the extravasal tissue. The uptake of the VSOP material is facilitated by its small size and a negative surface charge. Other suitable contrast agents that may be used instead of VSOP may be, for example, Supravist, Gadomer and Vasovist (all available from Bayer Schering, Leverkusen, Germany). Other appropriate blood-pool contrast agents may also be used.

Intravascular (blood pool) contrast agents normally remain substantially confined to the intravascular space, compared to Gd-DTPA, for example, which distributes or diffuses throughout the extracellular fluid space. This is a result of intravascular agents, which may be macromolecules, having a substantially higher molecular weight, compared to a molecular weight of 590 for Gd-DTPA.

In a method of evaluating treatment, the patient may be investigated with $T_1$ weighted DCE-MRI and subsequently with VSI. Also a combination of both applications using a slow-extravasating contrast agent can be considered.

MRI measurements may be performed using a clinical MRI system. Tumor morphology may be assessed using high resolution $T_1$ weighted GRE and $T_2$ weighted SE or turbo SE sequences. DCE-MRI may be performed using a dynamic $T_1$ weighted saturation recovery turbo FLASH (Fast Low Angle Shot) sequence. A contrast agent, such as Gadomer, may be injected during acquisition of, for example, the tenth dynamic image. Post-processing may be performed by pharmacokinetic modeling of contrast-enhanced dynamic data. Permeability-related constants can be quantified using a DCE analysis software package.

Vessel Size Imaging may be based on the susceptibility differences between vessels and the surrounding tissue, which is assessed by measuring the relaxation rate changes $\Delta R_2$ and $\Delta R_2^*$ induced by injection of an intravascular super-paramagnetic contrast agent. The vessel size index d may then be calculated using (1) or (4).

In an experiment, nude mice bearing squamous cell carcinoma xenografts were treated with an antiangiogenic therapy and investigated the therapy effects on DCE-MRI parameters and on VSI were investigated.

Seven nude mice bearing subcutaneous squamous cell carcinoma xenografts (HaCaT-ras-A5RT3), of which 4 were treated for 1 week with the VEGFR2 blocking antibody DC101 (800 µg/day), were investigated with $T_1$ weighted DCE-MRI and 24 hours later with VSI. MRI measurements were performed on a clinical 1.5 T whole-body MRI system (Siemens Magnetom Vision, Erlangen, Germany) using a custom-made active radiofrequency coil. Animal and tumor morphology were assessed using high-resolved $T_1$ weighted gradient echo sequences (FLASH) and $T_2$ weighted turbo spin echo sequences. DCE-MRI was performed using a $T_1$ weighed turbo FLASH sequence (TR 13 ms, TE 5.3 ms, TI 300 ms, Flip 12, averages 4, FOV 60×22.5, res. 0.5×0.5×2 mm$^3$). As a contrast agent, Gadomer (0.05 mmol/kg diluted in 0.9% NaCl to a total volume of 100 µl), was injected via the tail vein.

Post-processing was performed according to the two compartment model of Brix using a software program from DynaLab (from Mevis, Bremen, Germany), with a diffusion coefficient D of $10^{-3}$ m$^2$/s and a susceptibility difference $\Delta\chi$ of 0.571 ppm. $T_2$ weighted images (TSE, TR 3930 ms, TE 85 ms, averages 5, FOV 62×31, res. 0.5×0.5×1.5$^3$) were recorded and T2* determinations (FLASH 2D, TR 200, TE 6-24 ms, Flip 45°, averages 5, FOV 62×50, res. 0.5×0.5×1.5 mm$^3$) were performed before, and 3 min after, contrast agent (VSOP) administration.

The image data were analyzed using IDL (Research Systems Inc., Boulder, Colo.) and ImageJ. ImageJ is a public-domain Java image processing program inspired by NIH Image for the Macintosh computer. It runs, either as an online applet or as a downloadable application, on any computer with a Java 1.4 or later virtual machine. The author, Wayne Rasband, is at the Research Services Branch, National Institute of Mental Health, Bethesda, Md., USA.

Large liquid tumor areas, identified on $T_2$ weighted and $T_2^*$weighted images, were excluded from analysis of DCE-MRI and VSI scans. Differences in vessel density between treated and untreated tumors were also confirmed by immunofluorescence microscopy measuring area fractions of CD 31 positive vessels.

The amplitudes (A) of treated tumors (0.19±0.06) were found to be lower than those of untreated ones (0.42±0.16). The opposite results were obtained for $k_{ep}$, which was elevated in treated (0.70±0.31/min), as compared with untreated (0.36±0.15/min) tumors. These results did not differ with a suitable statistical significance. In contrast, differences in the VSI data were highly significant (p<0.002) as between untreated and treated tumors. The VSI of untreated and treated tumors was 0.25±0.01 mm and 0.35±0.03 mm, respectively. Histological analysis demonstrated the success of the antiangionic therapy and showed a reduction of vessel area fractions in treated tumors, which was particularly true for small vessels in the tumor centers (p<0.05)

The Vessel Size Imaging software program may execute as a stand-alone software package on a computer or on either the host of a MRI scanner, a satellite console, or a dedicated workstation.

FIG. 1 illustrates a magnetic resonance imaging (MRI) apparatus 1 which may be used to perform the therapy assessment in animals or humans. The apparatus 1 includes a magnet system 11 and gradient coils 12. These components provide magnetic fields used for magnetic resonance imaging. For magnetic field shimming purposes, a shimming coil 13 may be present. An antenna unit 14 sends radio frequency (RF) signals to an examination object (e.g., a patient 19 or an experimental animal), and for receiving a magnetic resonance signal emitted by the examination object. The examination object may be positioned in a field of view 18 of the apparatus 1 having a homogenous magnetic field by a movable patient bed 15. For controlling the magnetic resonance apparatus, a control unit 16 is present, which is connected to a computer 17 for entering measurement parameters and evaluating image data acquired by the apparatus 1.

Figure 2:
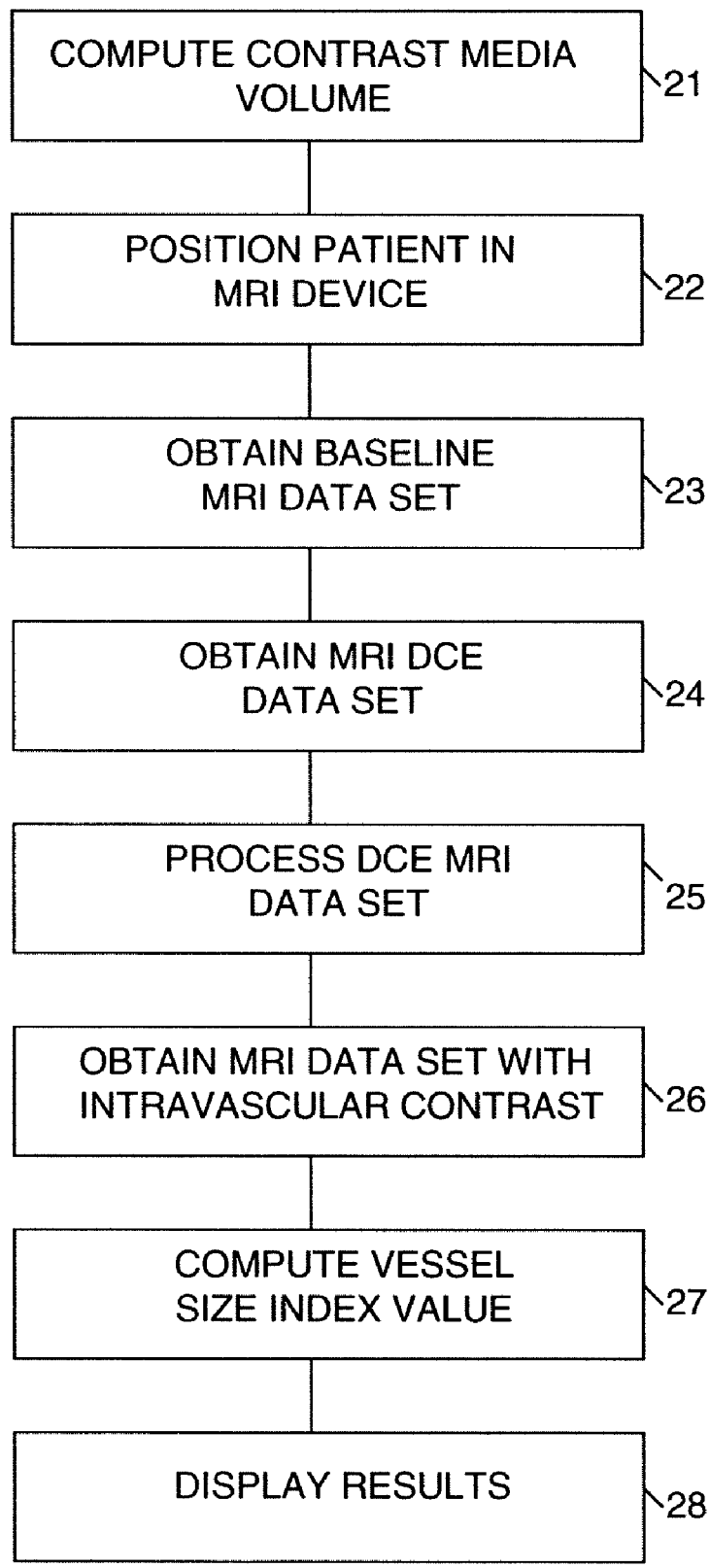
FIG. 2 is a block diagram illustrating a method for assessing anti-angiogenic therapy.

FIG. 2 illustrates steps in an example of the method. In describing the method, quantitative values are given for many of the specific MRI imaging functions. Such values are intended to provide a person of skill in the art with suggestions for adapting the method to the same or similar studies when using the other than the MRI device described herein. For the present MRI device, the values are indicative of parametric settings which may be useful in initial experimentation. Moreover, at the present time, acronyms are not fully standardized, and different manufacturers of MRI devices may use varying acronyms to describe the same or similar functions. Herein, where there is a conflict between the acronyms used, the acronym presently used by Siemens AG, at the time that this specification was prepared, is intended.

The volume of the contrast media to be administered is calculated with respect to the patient body weight (step 21). Standard values which may be used are 200 μmol Fe/kg body weight for VSOP or 50 μmol Gd/kg body weight for Gadomer. The concentration of the contrast agent may be changed without changing the DCE-MRI setup; however, a corresponding determination of $\Delta\chi$ for the VSI calculations may be needed. A first magnetic resonance data set of a patient is acquired using the MRI device after placement of an intravenous catheter and positioning of the patient in the MRI system (step 22). The first imaging step may be high-resolved $T_1$ weighted GRE, $T_2$ weighted SE and turbo SE sequences for tumor localization and assessment of tumor morphology.

For example, a $T_1$ quantification using a series of $T_1$ weighted saturation recovery turbo FLASH (fast low angle shot) (TR=17 ms, TE=7.06 ms, Flip=12°, Matrix: 128×64, Res.: 0.4×0.4×2 mm$^3$) sequences with different inversion times from 100 to 5000 ms may be performed (step 23). The $T_1$ quantification may be used for the DCE analysis and may also be used to choose an appropriate TR for the $T_2$ weighted SE sequences of the VSI experiment. To minimize $T_1$ effects in the $T_2$ weighted SE sequences, TR may be set to about five times $T_1$ of the tissue of interest, e.g. the tumor, leading to TR values up to about several seconds. Thus, quantification of T1 enables choosing the shortest TR that results in substantial exclusion of $T_1$ effects, and having optimal acquisition times.

The DCE-MRI data may then be obtained (step 24). For example, a dynamic series of $T_1$ weighted saturation recovery turbo FLASH sequences (TR=13 ms, TE=5.3 ms, TI=300 ms, Flip=12°, Matrix: 128×48, Res.: 0.5×0.5×2 mm$^3$, Averages=4) may be performed. Two single slice stacks are obtained: one positioned over the tumor, while the other is positioned over an artery to determine the arterial input function. This may be used for DCE-MRI analyses and to verify the correct contrast agent injection. Other $T_1$ weighted sequences may be used for acquisition of DCE-MRI data The contrast agent may be injected via the venous catheter during acquisition of, for example, the tenth dynamic image to obtain a correct baseline for the post-processing. Post-processing of DCE-MRI data (step 25) may be performed. Pharmacokinetic models may be applied to the dynamic data, for example, by using non-linear fitting algorithms, and allow the calculation of parameter maps with physiological relevant information, such as vessel permeability ($K_{trans}$), extra-vascular extra-cellular volume fraction ($V_e$), or vascular volume fraction ($V_p$).

User-defined regions-of-interest (ROI), may be employed to calculate and compare quantitative results for specific tissues-of-interest. Post-processing of DCE-MRI data may be performed before the VSI studies in a clinical situation as the absence of enhancement in the DCE-MRI data may be taken to imply that the vessels, if present, are not perfused. In this case the therapy success may be presumed and the examination can be stopped, so as to minimize patient exposure to radiation and reagents. If enhancement is detected in step 26, another MRI sequence may be performed to measure the relaxation rate changes $\Delta R_2^*$ and $\Delta R_2$ corresponding to the injection of the contrast agent. The measurement may consist of two imaging parts including, for example, $T_2$ weighted SE images (TR=6000 ms, TE=100 ms, averages=1, FOV: 60×50.4 mm$^2$, voxel size: 0.5×0.5×1.5 mm$^3$) and $T_2^*$ quantification before, and 3 min after administering the contrast agent. $T_2^*$ may be quantified, for example, by acquiring a series of $T_2^*$ weighted FLASH 2D images (TR=380 ms, TE=4.76-47.6 ms (10 in-phase echoes), Flip=45°, Averages=3, FOV: 62×50.4 mm$^2$, Res.: 0.5×0.5×1.5 mm$^3$) with different TEs. Optionally, in step 26, the apparent diffusion coefficient (ADC) may be determined for the vessel size index calculation (step 27) by diffusion weighted imaging. An SE echo planar imaging sequence may be performed (TR=3000 ms, TE=83 ms, Averages=4, Matrix: 64×64, Res.: 1×1×1.5 mm$^3$), In post-processing (step 27) the mean vessel size index d may be calculated using the data from the second MRI experiment using the Vessel Size Imaging analysis program. After data import and fast data inspection the vessel size index d may be calculated by equation (1), where D is the diffusion coefficient, γ is the gyromagnetic ratio, $\Delta\chi$ is the susceptibility difference between blood vessel and surrounding tissue, and $B_0$ is the magnetic field strength. If δω instead of $\Delta\chi$ is known for the used contrast agent, the vessel size index d may be calculated by equation (4)

The changes in relaxation rate $\Delta R_2$ can be calculated from the SE (TR=6000 ms, TE=100 ms, averages=1, FOV: 60×50.4 mm$^2$, voxel size: 0.5×0.5×1.5 mm$^3$) measurements by taking the natural logarithm of the relative signal intensities from post- and pre-contrast images divided by the echo time $T_E$, using equation (2).

$\Delta R_2^*$ maps may be calculated from $T_2^*$ weighted GRE (TR=380 ms, $T_E$=4.76-47.6 ms (10 in-phase echoes), Flip=45°, Averages=3, FOV: 62×50.4 mm$^2$, Res.: 0.5×0.5×1.5 mm$^3$) images acquired with increasing $T_E$, using equation (3).

$\Delta R_2^*$ maps may be obtained by fitting an exponential decay function vs. $T_E$ to voxel in the pre contrast response-post contrast $T_2^*$ weighted image series and subtracting the $R_2^*$ fit parameter post- and pre-contrast for each voxel being analyzed. The diffusion constant D may either be assumed to be constant over the whole imaged volume, or taken from the apparent diffusion coefficient (ADC) maps obtained from diffusion weighted imaging in step 26*a*.

The results of the post-processing steps 23 and 27 may be presented to the user for assessing the therapy response (step 28). In another aspect automatic evaluation of the therapy response is performed and the result is presented to the user.

In either embodiment the visualization may include a display of parametric maps which overlay the calculated physiologic parameter and anatomical information pixel by pixel.

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically claimed herein, the order and grouping of steps and the parametric values are not a limitation of the present invention.

A computer program product is described for processing DICOM (Digital Communications in Medicine) images and extracts needed parametric information form the DICOM header. The DICOM data may be retrieved from a data base over a network.

Images may be displayed simultaneously, allowing quick navigation through images and fast inspection of data quality of measured images. The quality of fitting of the data can be assessed on maps or by displaying fitting curves with data curves for individual voxel assessment. The accuracy of parametric maps may be improved by using a filter algorithm to exclude voxels with low agreement between fit and data curves. Segmentation of the images may allow the calculation of quantitative values for a specific tissue type of interest. A load-and-save function for region-of-interest (ROI) information may facilitate repeated analyses for each data set.

The parametric images may be exported to an image data base so that vessel size index or BV maps may be used for further processing or visualization steps, such as fusion with anatomical images: for example, using Syngo®, available from Siemens, Munich, Germany.

For visualizing data, setting MRI parameters, and controlling aspects of the treatment and analysis a data interface, as is known in the art, may be provided. The interface may be a visual display, keyboard data entry device, computer mouse, touch screen, or the like.

The apparatus and method can also be used in pharmaceutical research and the development of pharmaceuticals. In this case, the methods are typically applied to animals, e.g. mice, using small animal imaging.

The apparatus and method can also be used for tissue differentiation, such as identification of cicatrizes or relapse after tumor resection, tumor staging and classification.

The examples of diseases, syndromes, conditions, and the like, and the types of examination and treatment protocols described herein are by way of example, and are not meant to suggest that the method and apparatus is limited to those named, or the equivalents thereof. As the medical arts are continually advancing, the use of the methods and apparatus described herein may be expected to encompass a broader scope in the diagnosis and treatment of patients.

It is intended that the foregoing description be regarded as illustrative rather than limiting, and that it be understood that it is the following claims, including all equivalents, that are intended to define the spirit and scope of this invention.

What is claimed is:

1. A method of assessing angiographic therapy, the method comprising:
   placing a subject in a magnetic resonance imaging (MRI) device;
   acquiring a dynamic contrast enhanced (DCE) MRI data set;
   administering a blood pool contrast agent via a venous catheter during the acquisition of the DCE MRI data set;
   obtaining an MRI image sequence data set after obtaining the DCE MRI data set; and
   determining a vessel size index value before and after the angiographic therapy with a therapeutic agent, wherein determining the vessel size index value comprises using a susceptibility difference between blood vessels and tissue surrounding the blood vessels or using a spread of a Larmor frequency.

2. The method of claim 1, wherein a volume of the blood pool contrast agent administered is proportional to a body weight of the subject.

3. The method of claim 1, wherein the blood pool contrast agent comprises nanoparticles.

4. The method of claim 1, wherein the blood pool contrast agent comprises macromolecules.

5. The method of claim 1, wherein the blood pool contrast agent comprises a diffusible contrast agent.

6. The method of claim 1, further comprising evaluating the DCE MRI data set,
   wherein evaluation of the DCE MRI data set comprises the application of pharmacokinetic models to the DCE MRI data set.

7. The method of claim 1, wherein the vessel size index value is parametric in a ratio of a change in a $T_2^*$ weighted image relaxation rate to a change in a $T_2$ spin echo image relaxation rate.

8. The method of claim 1, wherein during the obtaining of the MRI image sequence data set, transversal relaxation rates $R_2$ and $R_2^*$ are measured before and after administering the blood pool contrast agent.

9. The method of claim 1, further comprising assessing a relative effectiveness of the therapeutic agent using the vessel size index value.

10. The method of claim 1, wherein the DCE MRI data set and the vessel size index value are used to evaluate the effectiveness of the therapy.

11. A method for treating a patient, the method comprising:
    acquiring a dynamic contrast enhanced (DCE) MRI data set;
    administering, via a catheter, an intravascular contrast agent during the acquisition of the DCE MRI data set;
    obtaining an MRI data set after obtaining the DCE MRI data set, the MRI data set suitable for performing a vascular size imaging analysis;
    determining, by a processor, a vessel size index value before and after therapy with a therapeutic agent, wherein determining the vessel size index value comprises using a susceptibility difference between blood vessels and tissue surrounding the blood vessels or using a spread of a Larmor frequency in the vascular size imaging analysis; and
    performing, by the processor, the vascular size imaging analysis, wherein performing the vascular size imaging analysis comprises measuring a first parameter proportional to a volume of a microvascular network in a region of interest and measuring a second parameter proportional to a volume of all of the blood vessels in the region of interest.

12. The method of claim 11, further comprising determining an effectiveness of a treatment of the patient based on a ratio of the first parameter to the second parameter.

13. A method of assessing angiographic therapy, the method comprising:
acquiring a dynamic contrast enhanced (DCE) MRI image data set;
injecting, via a catheter, an intravascular contrast agent during the acquisition of the DCE MRI image data set;
acquiring an MRI image data set after obtaining the DCE MRI image data set;
storing the DCE MRI image data set and the MRI image data set in a database;
presenting the DCE MRI and MRI image data sets stored in the database at a user interface; and
determining a vessel size index value to assess an effectiveness of a therapeutic agent used in a treatment of a patient,
wherein determining the vessel size index value comprises using a susceptibility difference between blood vessels and tissue surrounding the blood vessels or using a spread of a Larmor frequency.

14. The method of claim 13, wherein storing comprises storing the DCE MRI image data set and the MRI image data set in a database accessible over a network.

15. The method of claim 14, wherein the DCE MRI and MRI image data sets are compatible with digital communications in medicine (DICOM).

* * * * *